United States Patent
Negus et al.

(12)

(10) Patent No.: US 6,241,665 B1
(45) Date of Patent: Jun. 5, 2001

(54) PERCUTANEOUS MAPPING SYSTEM

(75) Inventors: Charles Christopher Negus, Taunton; Robert R. Andrews, Norfolk; Stephen J. Linhares, Taunton; Robert I. Rudko, Holliston; Eileen A. Woodruff, Whitinsville, all of MA (US)

(73) Assignee: PLC Medical System, Inc., Franklin, MA (US)

( * ) Notice: Subject to any disclaimer, the term of this patent is extended or adjusted under 35 U.S.C. 154(b) by 0 days.

(21) Appl. No.: 09/176,506

(22) Filed: Oct. 21, 1998

(51) Int. Cl.[7] .................................................... A61B 5/00
(52) U.S. Cl. ............................................. 600/374; 607/89
(58) Field of Search .................... 600/585, 374; 607/1, 2, 89, 92, 93, 98, 99, 116, 122; 606/41, 14

(56) References Cited

U.S. PATENT DOCUMENTS

| | | | |
|---|---|---|---|
| 5,156,151 | * 10/1992 | Imran | 607/122 |
| 5,239,999 | * 8/1993 | Imran | 607/127 |
| 5,324,284 | 6/1994 | Imran . | |
| 5,409,000 | 4/1995 | Imran . | |
| 5,464,404 | 11/1995 | Abela et al. . | |
| 5,509,411 | 4/1996 | Littmann et al. . | |
| 5,645,064 | 7/1997 | Littmann et al. . | |
| 5,680,860 | * 10/1997 | Imran | 600/585 |
| 5,682,885 | 11/1997 | Littmann et al. . | |
| 5,730,741 | 3/1998 | Horzewski et al. . | |
| 5,938,694 | * 8/1999 | Jaraczewski et al. | 607/122 |

FOREIGN PATENT DOCUMENTS

PCT/US97/
05714    10/1997  (WO) .

* cited by examiner

*Primary Examiner*—Kennedy Schaetzle
(74) *Attorney, Agent, or Firm*—Iandiorio & Teska

(57) ABSTRACT

A percutaneous mapping system includes a mapping wire, for percutaneous insertion into an internal body cavity, having a plurality of spaced imaging markers; and an insertion device for deploying the mapping wire in a spiral configuration inside the cavity with the markers distributed about the inner wall of the cavity.

3 Claims, 8 Drawing Sheets

MARKER WIRE DEPLOYED IN LEFT
VENTRICLE WITH TREATMENT CATHETER

MARKER WIRE PLACED IN LEFT VENTRICLE WITH GUIDEWIRE

MARKER WIRE DEPLOYED IN LEFT VENTRICLE WITH GUIDEWIRE

MARKER WIRE DEPLOYED IN LEFT VENTRICLE WITH TREATMENT CATHETER

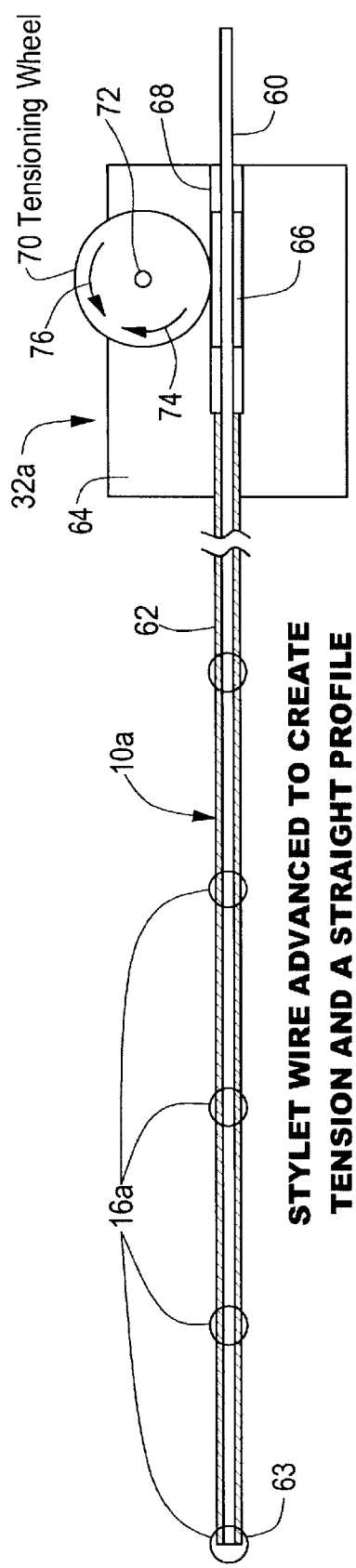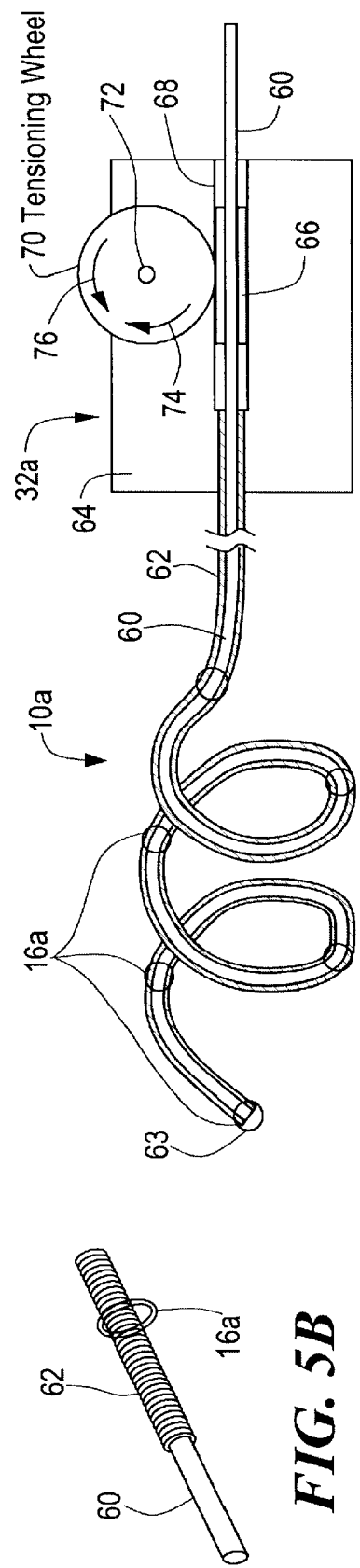

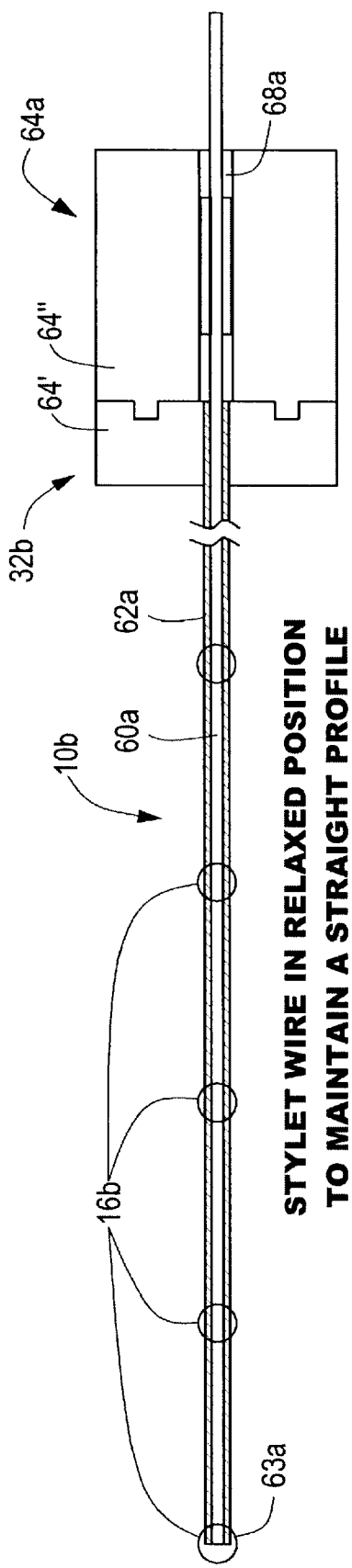
FIG. 7 STYLET WIRE IN RELAXED POSITION TO MAINTAIN A STRAIGHT PROFILE
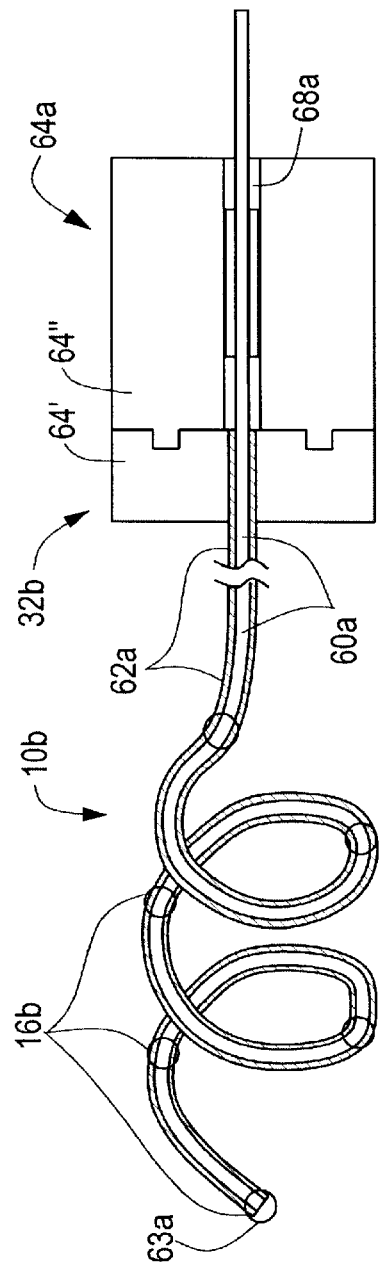
FIG. 8 STYLET WIRE TORQUED TO CREATE A SPIRAL CONFIGURATION

MULTIPLE SENSORS

SENSOR

MAPPING WIRE WITH CONTROL SYSTEMS

PERCUTANEOUS MAPPING SYSTEM

FIELD OF INVENTION

This invention relates to an improved percutaneous mapping system and one which can be used to sense the location of ischemic regions in the heart or the presence of an instrument in a body cavity.

BACKGROUND OF INVENTION

Chronic angina pectoris is a very common disease in the United States. Currently, the most common methods of reperfusing ischemic myocardium are cardiac arterial bypass graft (CABG) and percutaneous transluminal coronary angioplasty (PTCA) operations, with 330,000 and 500,000 such procedures performed every year in the United States. Both techniques restore blood flow to the ischemic myocardium by bypassing or removing the atherosclerotic lesions which obstruct blood flow. However, despite advances in treatment techniques, there is a large group of patients who cannot undergo CABG or PTCA due to severe diffuse coronary atherosclerotic disease.

The concept of supplying blood to a myocardium devoid of the natural arterial network is not new. It was discovered many years ago that reptiles have no major coronary arteries and that their hearts are nourished by channels that supply blood directly from the heart chambers into the myocardium.

By creating such channels in ischemic human myocardium, it is possible to bring arterial blood, and therefor oxygen, directly into the deep endocardial layer of the heart muscle. Several investigators have attempted to duplicate the reptilian system in human hearts with techniques that ranged from the Vineberg procedure (implanting the left internal mammary artery into the myocardium) to the making of myocardial channels through needle acupuncture. These attempts resulted in temporary increases in myocardial protection and perfusion due to blood flow through the channels but were eventually unsuccessful as the channels quickly closed as a result of the mechanical trauma associated with these procedures. These investigations nevertheless proved that transmyocardial revascularization (TMR) was capable of creating direct blood pathways from the ventricle into the myocardium. They also demonstrated that long term success of TMR depended upon the method used to create the transmural channels.

A high power pulsed $CO_2$ laser can create small diameter ($\leq 1$ mm) transmyocardial channels in less than 100 milliseconds. The laser energy vaporizes myocardial tissue along its path before being stopped by the blood present in the ventricle. This vaporization process is so fast that it does not cause thermal or mechanical damage to the surrounding tissue, thereby creating virtually char-free channels of long term patency. More specifically, the epicardial channel entry site quickly seals off under the finger pressure of the surgeon while the remaining section of the channel remains open and permits oxygenated blood flow directly into the ischemic myocardium.

There are three principal surgical approaches potentially available for TMR, open chest surgery, minimally invasive surgery and the percutaneous approach. In an open chest TMR procedure, the heart is exposed by a cardiovascular surgeon typically by a left thoracotomy. The procedure is performed epicardially (from outside the heart into the left ventricle) on the beating heart. Typically 20 to 30 channels are formed in the ischemic regions of the left ventricle. A minimally invasive TMR procedure is accomplished by using video assisted thoracoscopic surgery. The surgeon makes four incisions between the ribs, two for endoscopic instruments, one for the thoracoscope (telescope/monitoring system) and one for the laser handpiece. The pericardium is removed from the region to be treated and the channels are then formed in the left ventricle. A percutaneous myocardial revascularization (PMR) system would be used by an interventional cardiologist in a cardiac catheterization laboratory. This interventional cardiologist would access the heart through an artery and advance a catheter based PMR delivery system through the aorta and into the left ventricle. Once the catheter tip entered the ventricle, it would be guided to the ischemic regions of the endocardial surface to create channels that would pass partially through the wall of the heart.

A basic factor which must be addressed in developing a percutaneous system is the location of the catheter tip. The three dimensional location of the of the device and subsequent location of the channels formed is critical so that the channels are located in the ischemic regions at properly spaced intervals. A feature of a percutaneous myocardial revascularization system (PMR) is determining the location of the tip of the catheter and the subsequent location of the channel formed. The channels should be formed in the ischemic region of the left ventricle. Spacing of the channels at 1 cm intervals prevents creating multiple channels in one location and potentially perforating the outer wall of the ventricle causing tamponade. Spacing of the channels provides a network of channels for even reperfusion of the ischemic region.

Mapping of the heart can be accomplished by several techniques. Fluoroscopic X-ray will produce a two dimensional view (see U.S. Pat. Nos. 5,558,091 and 5,568,809) which will not provide a precise location of the catheter tip. Electromagnetic sensors could be utilized; however, additional equipment would be required to determine the location. Ultrasound trans-esophogeal echocardiogram (TEE) provides a view of a channel but it would not provide a view of multiple channels simultaneously.

In U.S. Pat. No. 5,730,741, a spiral member is shown which can be used to map the inside of an organ, but the treatment catheter is constrained to follow the spirals of the spiral member resulting in a loss of power as well as increased difficulty in guiding the catheter along the spiral configuration. Moreover, this configuration can cause a change in the modality of the transmitted laser beam and serious heating of the optical fiber itself. Also, the tip of the catheter is constrained to be positioned only where the spiral member is located within the organ.

SUMMARY OF INVENTION

It is therefore an object of this invention to provide an improved percutaneous mapping system.

It is a further object of this invention to provide such a mapping system which is simple and inexpensive.

It is a further object of this invention to provide such a mapping system which is usable with existing imaging equipment.

It is a further object of this invention to provide such a mapping system which provides a basic frame of reference for visualizing the position of a catheter or other instrument in a human body cavity.

It is a further object of this invention to provide such a mapping system which enables the detection of ischemic regions and the presence of instruments or foreign bodies in a human body cavity.

The invention results from the realization that a truly simple and effective percutaneous mapping system can be achieved using a wire having a plurality of spaced imaging markers for percutaneous insertion into a body cavity in a spaced configuration with the markers distributed about the inner wall of the cavity, and the further realization that by associating with the markers sensor devices for sensing the electrical potential of the cavity wall in the vicinity of the marker, the presence of ischemic and foreign bodies can be detected.

This invention features a percutaneous mapping system including a mapping wire, for percutaneous insertion into an internal body cavity, having a plurality of spaced imaging markers and an insertion device for deploying the mapping wire in a spiral configuration inside the cavity with the markers distributed about the inner wall of the cavity.

In a preferred embodiment the wire may be preformed in a spiral shape and the insertion device may include means for advancing the wire in straight shape into the cavity and releasing it there to assume its spiral shape. The wire may be straight and the insertion device may include means for advancing the wire into the cavity and torquing it to assume a spiral shape in the cavity. The imaging markers may be radiopaque, ultrasonically sensible or electromagnetically sensible. The imaging marker may include a sensor device for sensing the electrical potential at the wall of the cavity proximate that imaging marker. The sensing device may include a pair of spaced electrodes. The image markers may have different shapes. There may be means responsive to the electric potential for determining the presence of ischemia and there may be means responsive to the electric potential for determining the presence of a foreign body proximate the cavity wall in the vicinity of the sensor device.

DISCLOSURE OF PREFERRED EMBODIMENT

Other objects, features and advantages will occur to those skilled in the art from the following description of a preferred embodiment and the accompanying drawings, in which:

FIG. 5A is a side elevational schematic diagram with parts in section of the control device of FIGS. 2, 3 and 4 with the spirally preformed mapping wire tensioned to a straight shape;

FIG. 5B is a three-dimensional view showing the composite structure of he mapping wire including an internal stylet and an external sheath;

FIG. 6 is a view similar to FIG. 5 with the mapping wire untensioned and assuming its spiral configuration;

FIG. 7 is a view similar to FIGS. 5 and 6 of an alternate construction of the control device of FIGS. 2, 3 and 4 including a straight preformed mapping wire and a torquing mechanism;

FIG. 8 is a view similar to FIG. 7 after the straight preformed mapping wire has been torqued into a spiral shape;

Figure 1:
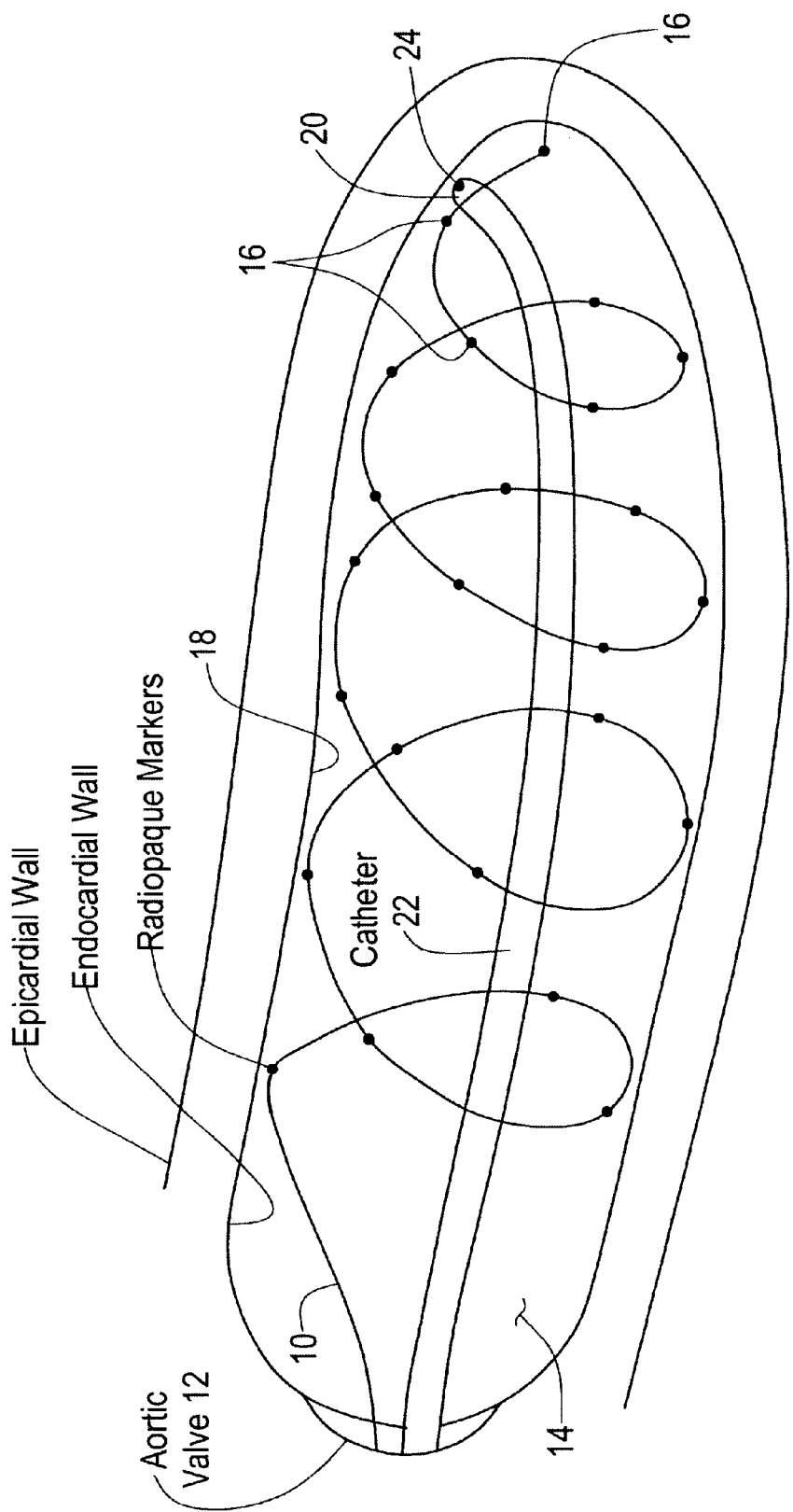
FIG. 1 is an enlarged three-dimensional schematic diagram of a mapping wire spirally disposed in the left ventricle of a heart and accompanied by a treatment catheter.

There is shown in FIG. 1 a mapping wire according to this invention including a mapping wire or filament 10 extending in a spiral configuration through aortic valve 12 into left ventricle 14 of a heart. Spaced along mapping wire 10 are a plurality of imaging markers 16 which by virtue of the spring force of the spirally disposed wire 10 are pressed against the endocardial or inner wall 18 of ventricle 14. Each of the imaging markers 16 is formed of a material which is sensible by the particular type of radiation being used for the imaging. For example, if the imaging is using a fluoroscope or X-ray technique then markers 16 would be radiopaque. If used in an electromagnetic sensing system such as in U.S. Pat. Nos. 5,558,091 and 5,568,809, they will be magnetic material; if ultrasonic they would be an ultrasonic sensible material such as a hollow sphere. With the proper illumination and display, then, an image showing markers 16 in ventricle 14 would appear on a screen and the position of the tip 20 of treatment catheter 22 could be easily visualized with respect to the various markers. Thus if treatment catheter 22 contains an optic fiber for transmitting a laser beam such as a $CO_2$ laser beam to and out of treatment tip 20 for performing percutaneous myocardial revascularization, for example, an additional marker 24 could be inserted in tip 20 so that its position relative to the various markers 16 could be easily visualized. In that way channels could be cut by the laser beam safely and properly spaced. As shown, catheter 22 is separate from mapping wire 10 and thus is not constrained to follow its spiral configuration which would result in a loss of laser energy, power, and the inability to lase the heart wall at locations when the wire is not touching the inner wall of the ventricle. Since catheter 22 is not bent into a spiral shape, there is no heating of catheter 22 and no modal changes in the laser energy. Also, the difficulty of guiding the catheter along a spiral configuration is eliminated.

Figure 2:
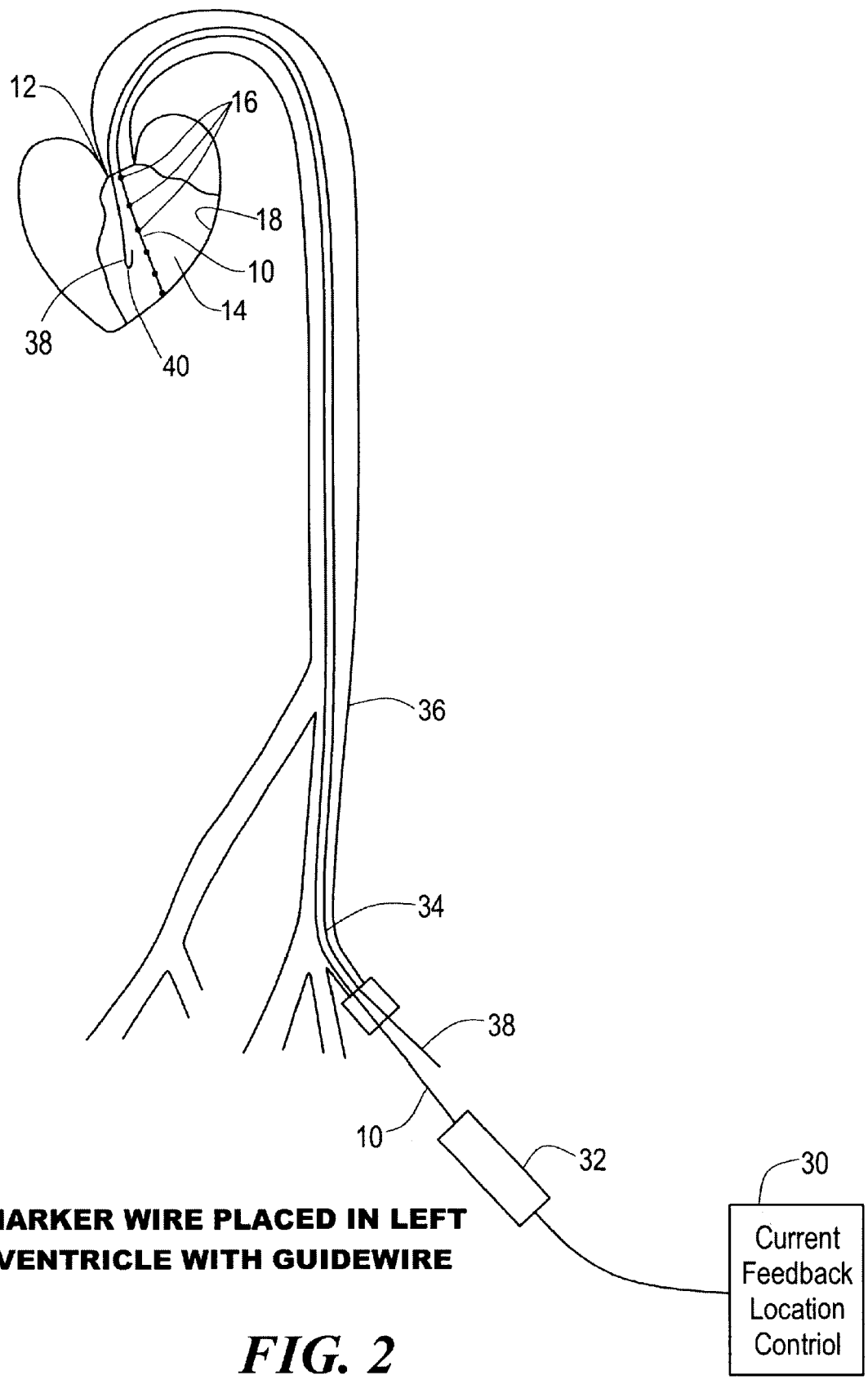
FIG. 2 is a schematic diagram of a mapping wire and a guide wire installed through an introducer sheath into and through an artery into the left ventricle of the heart with the mapping wire in the straight condition.

Markers 16 may, in addition to being sensible for a particular type of imaging radiation, may also include sensors for detecting the electric potential at the inner wall 18 of ventricle 14 in the vicinity of the particular marker or sensor 16. The electric potential sensed is fed back to a voltage feedback location control circuit 30, FIG. 2, which is connected through control device 32 to mapping wire 10 which is installed through an introducer sheath 34 into an artery 36 through aortic valve 12 and into ventricle 14. Wire 10 is shown in the straight form in ventricle 14 in FIG. 2. Accompanying wire 10 in ventricle 14 is a guide wire 38 which contains a small J hook 40 on its end for ease of insertion.

Figure 3:
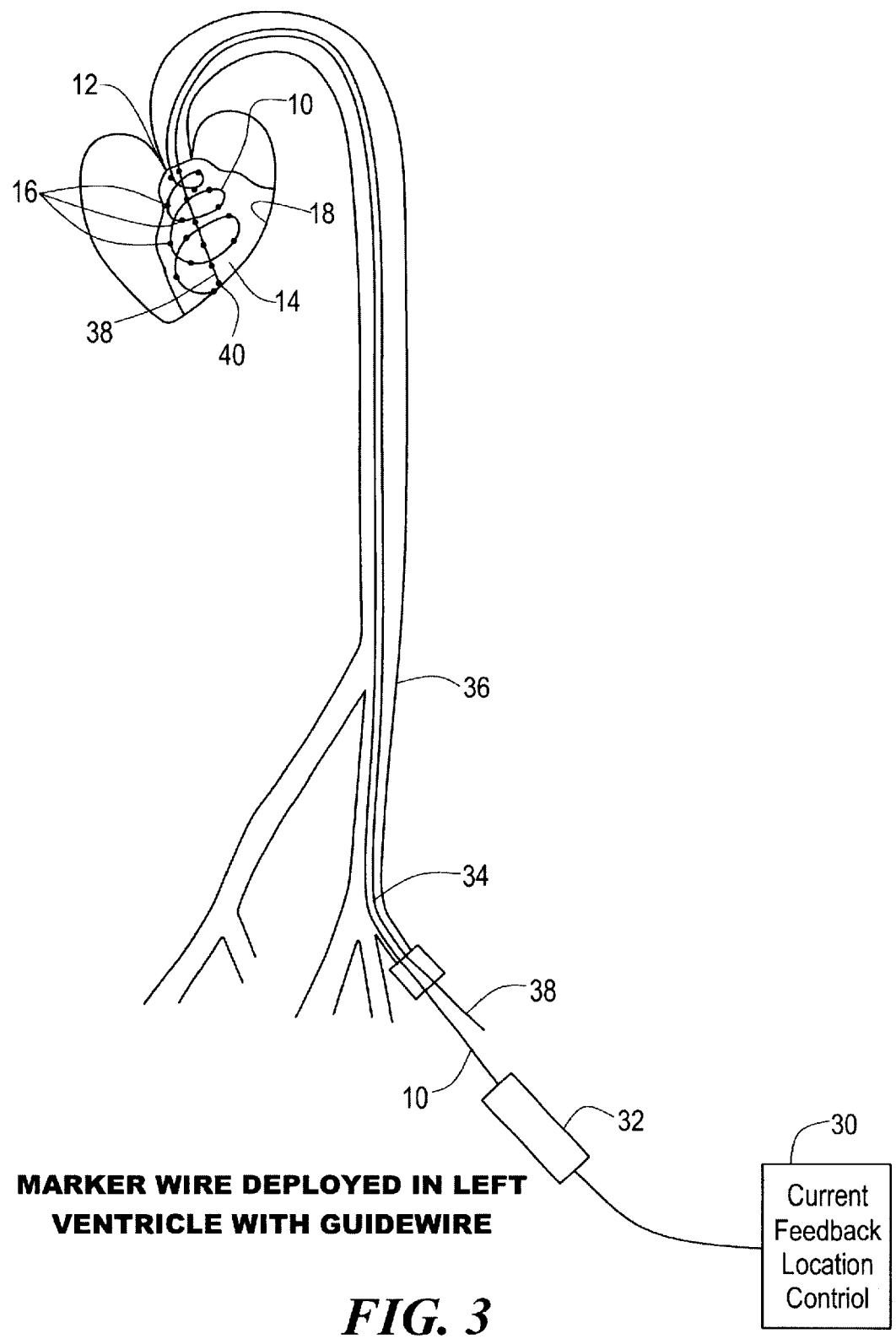
FIG. 3 is a view similar to FIG. 2 with the mapping wire disposed in a spiral configuration.
Figure 4:
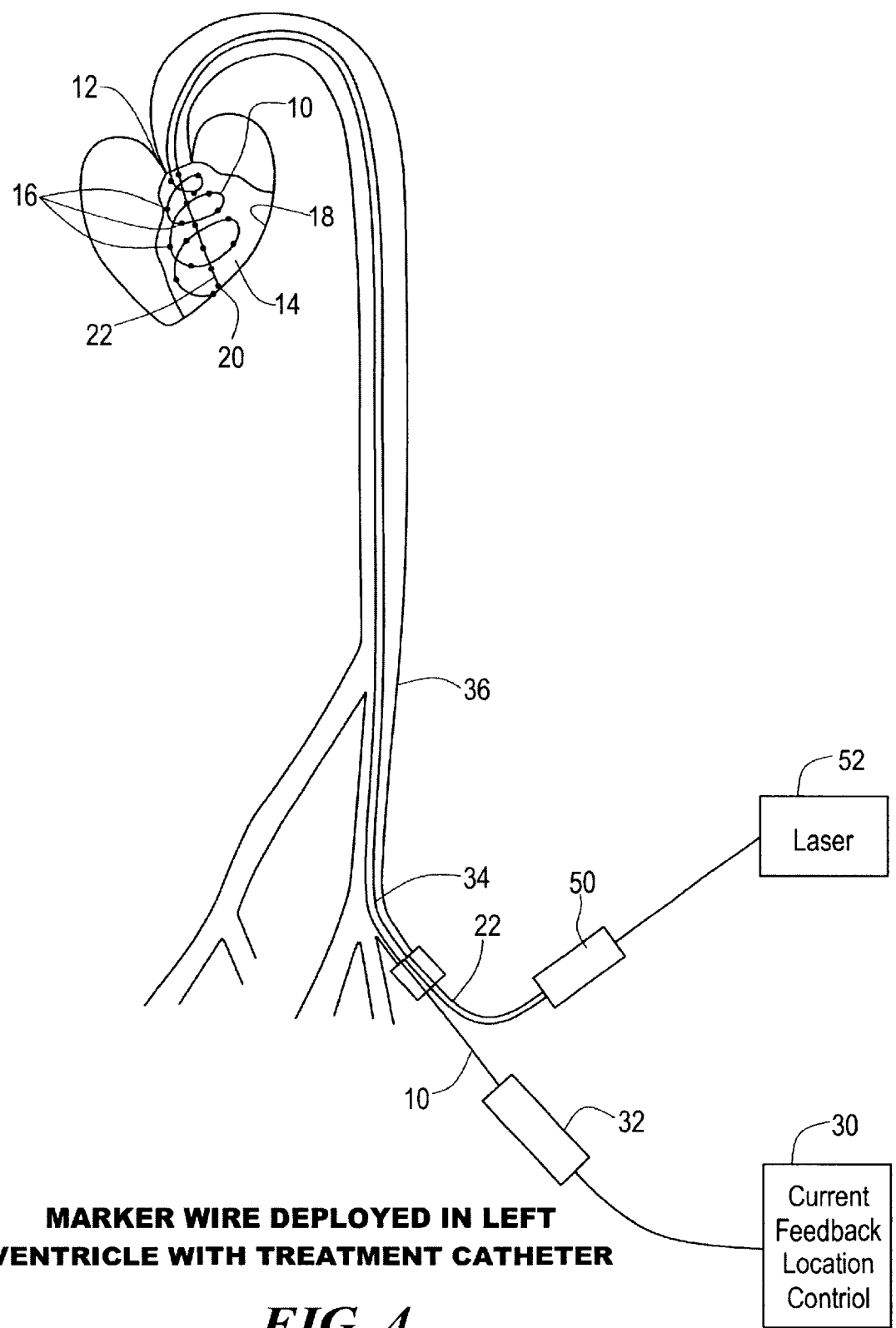
FIG. 4 is a view similar to FIGS. 2 and 3 with a PMR catheter including a laser delivery optic fiber introduced through the artery into the left ventricle of the heart.

After map wire 10 has been deployed in the spiral shape, as shown in FIG. 3, a treatment catheter 22 is installed over guide wire 38 and guide wire 38 is withdrawn. The position of treatment catheter 22 is controlled by catheter control 50 and receives the laser input beam from laser 52 in FIG. 4. Such a laser driven transmyocardial revascularization system synchronized with the heart is shown in U.S. Pat. No.

5,125,926. Wire 10 may be formed at least partially from superelastic or shape memory materials as disclosed in U.S. Pat. No. 5,730,741 incorporated herein by this reference.

Alternatively, wire 10*a* includes two parts: an internal solid filament or stylet 60, FIG. 5A, and an outer or external sheath 62 which may be a braid or coil as shown in FIG. 5B, where the solid stylet 60 is shown surrounded by a continuous coil 62. Markers 16*a* are mounted on the external sheath 62 which at its inner end is fixed to housing 64 of control device 32*a*. Stylet 60 extends through sheath 62 and mounts to a cylindrical slider 66 in bore 68 of housing 64. A tensioning wheel 70 rotatable about axis 72 and typically made of rubber or some other elastomeric material frictionally engages cylinder 66 and drives it forward and back depending upon the direction of rotation of wheel 70. Stylet 60 is fixed to sheath 62 at the distal end 63 and has been preformed to have a coiled or spiral shape. Thus in FIG. 5A thumb wheel 70 has been rotated clockwise in the direction of arrow 74 to push stylet 60 forward in sheath 62. This removes the coil or spiral shape of stylet 60 and holds it in a straight shape. The friction of wheel 70 is sufficient to keep cylindrical slide 66 in position with stylet 60 so tensioned. After wire 10*a* has been inserted into the ventricle of the heart, wheel 70 may be released by rotating it in the counterclockwise direction as indicated at arrow 76 so that the stylet is free to collapse and reassume its coiled or spiral shape as shown in FIG. 6.

Alternatively, stylet 60*a*, FIG. 7, may have a generally straight shape, outer sheath 62*a* may be fixed to first portion 64' of housing 64*a* and stylet 60*a* may be fastened to the second portion 64" of housing 64*a* of control device 32*b*. In the condition shown in FIG. 7 stylet 60*a* and sheath 62*a* are extended and straight as they will be when introduced into the ventricle of the heart. After they are in the ventricle of the heart, parts 64' and 64" are rotated relative to one another to torque the inner stylet 60*a* with respect to the sheath 62*a*. This causes the wire 10*b* to twist and form a spiral shape in the ventricle as shown in FIG. 8.

Figure 10:
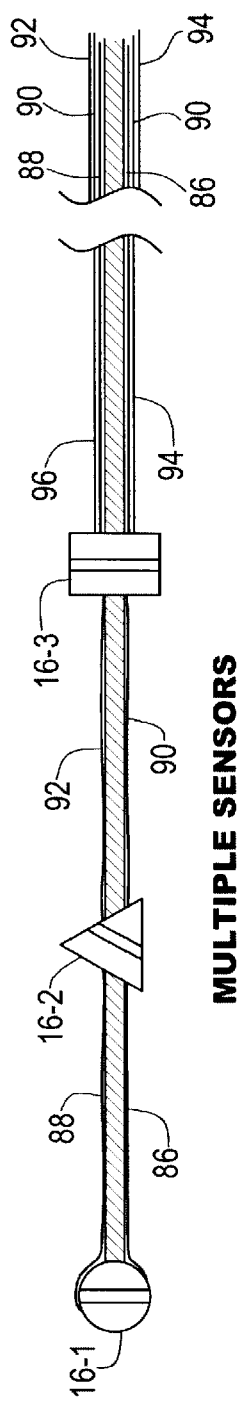
FIG. 10 is an enlarged detailed side sectional schematic view of a portion of the mapping wire showing a number of different shaped markers installed thereon.
Figure 9:
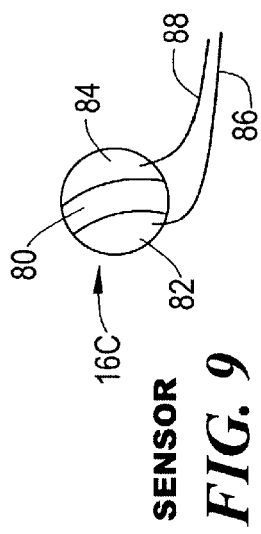
FIG. 9 is a three-dimensional view of a single marker device which includes an electric field sensing device.

Imaging markets 16, 16*a* and 16*b* may include not just a radiopaque or other image sensible material 80, FIG. 9, but may include some means for sensing the electric potential in the area of the endocardial wall that it touches. For example, marker 16*c*, FIG. 9, may include on either side of the image sensible medium 80 a pair of electrodes 82, 84 which will sense the electric potential on either side of the medium 80 which for example could be a radiopaque insulating medium such as barium sulfate filled polyvinyl chloride. Marker 16*c* has leads 86, 88 which extend from electrodes 82 and 84 back to the current feedback location control 30. The markers may have distinctly different shapes so that adjacent markers can be distinguished and the true position of the marker in the ventricle, viewed through fluoroscopy or some other means, can be easily seen. For example, as shown in FIG. 10, the first marker 16-1 is spherical; the next marker 16-2 is triangular in shape; the next marker 16-3 is rectangular in shape. Different shapes may be used for the succeeding markers or the pattern of spherical, triangular and rectangular could be repeated again and again so that at least neighboring markers could be distinguished. Each of the markers 16-1, 16-2, 16-3 has its own pair of leads 86, 88, 90, 92, 94, 96, respectively, which feed back to current feedback location control 30 shown in FIGS. 2, 3 and 4.

Figure 11:
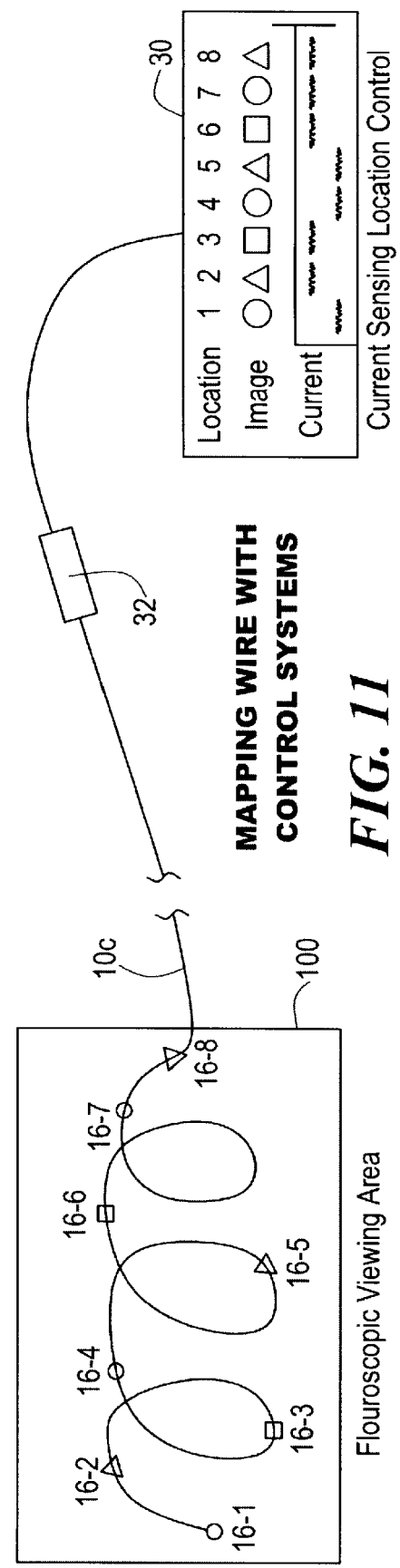
FIG. 11 is a schematic block diagram of a system which senses and displays the electric field in the vicinity of each of the markers.
Figure 12:
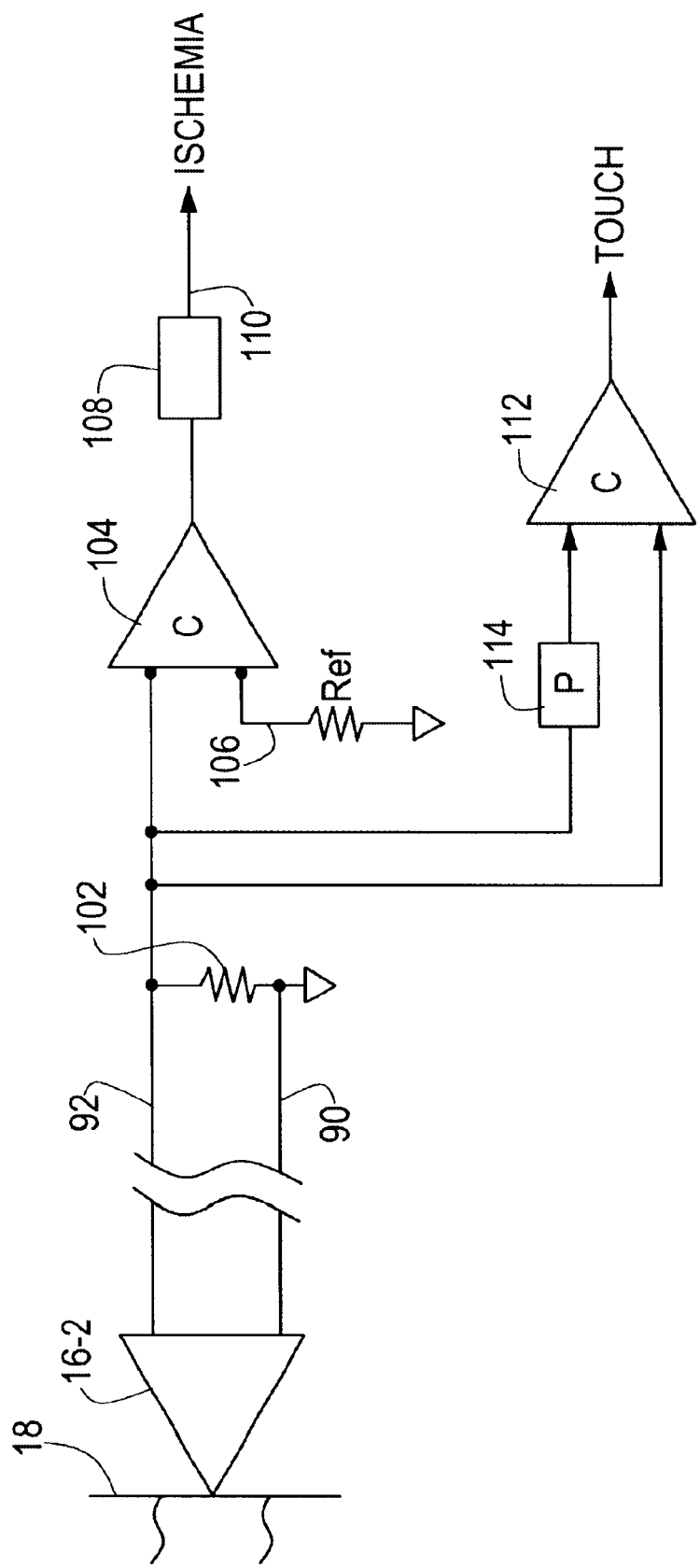
FIG. 12 is a schematic diagram of a circuit for detecting ischemic regions and/or the presence of a foreign object in the vicinity of a marker.

In one illustrative example, eight markers 16-1 through 16-8, FIG. 11, are viewable in fluoroscopic viewing area 100. All of the leads from the electrodes are fed from the control device 32 to current sensing location control circuit 30 which for example displays on it the numbers of the markers 1, 2, 3, 4, 5, 6, 7, 8 in the row marked Location, and beneath it in the row marked Image, the indication of the shape of that particular marker: round, triangular, rectangular, repeated over and over again in that sequence of three. In the last row, the voltage level being sensed by the electrodes associated with that marker is indicated. A high level of voltage generally would indicate a healthy portion of the heart in the vicinity of that marker; a low might indicate ischemia or perhaps the presence of a foreign body such as the tip of the treatment catheter in that vicinity. A particular marker 16-2, FIG. 12, senses a particular voltage at the endocardial wall and provides a voltage over leads 90, 92. That voltage is delivered to comparator 104 along with a reference voltage from reference 106. The output of comparator 104 is delivered to a threshold circuit 108. If the output of comparator 104 is below a certain level then an indication of ischemia may be provided on output line 110. The same signal fed to comparator 104 may be fed directly to one input of comparator 112 and through a delay line 114 through the other input of comparator 112. Then if there is a decrease in voltage between the current signal and the delayed signal the output can indicate that the endocardial wall has been touched by a foreign object such as the tip of the catheter or that ischemia has occurred.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A percutaneous mapping system comprising:

a catheter for percutaneous insertion into an internal body, the catheter including a treatment tip;

a separate mapping wire for percutaneous insertion into an internal body cavity, the wire having a plurality of spaced imaging markers; and an inserting device for deploying said mapping wire in a spiral configuration inside said cavity with said markers distributed about the inner wall of said cavity for mapping the cavity and determining the position of the tip of the catheter within the body, wherein said wire includes a straight stylet and said insertion device includes an outer sheath means surrounding and fixed to said stylet at its tip and bearing said image marker means for advancing the wire with said stylet in a straight shape into the cavity and torquing it to assume a spiral shape in the cavity.

2. A percutaneous mapping system comprising:

a catheter for percutaneous insertion into an internal body, the catheter including a treatment tip;

a separate mapping wire for percutaneous insertion into an internal body cavity, the wire having a plurality of spaced imaging markers; and an inserting device for deploying said mapping wire in a spiral configuration inside said cavity with said markers distributed about the inner wall of said cavity for mapping the cavity and determining the position of the tip of the catheter within the body, wherein at least one of said plurality of spaced imaging markers includes a sensor device for sensing the electric potential at the wall of the cavity proximate said at least one imaging marker, and wherein said plurality of spaced image markers have different shapes.

3. A percutaneous mapping system comprising:

a catheter for percutaneous insertion into an internal body, the catheter including a treatment tip;

a separate mapping wire for percutaneous insertion into an internal body cavity, the wire having a plurality of spaced imaging markers, at least one of said plurality of spaced imaging markers including a sensor device for sensing the electric potential at the wall of the cavity proximate said at least one imaging marker;

an inserting device for deploying said mapping wire in a spiral configuration inside said cavity with said markers distributed about the inner wall of said cavity for mapping the cavity and determining the position of the tip of the catheter within the body; and means responsive to the electric potential for determining the presence of a foreign body proximate the cavity wall in the vicinity of the sensor device.

* * * * *